(12) United States Patent
Sun et al.

(10) Patent No.: US 8,389,763 B2
(45) Date of Patent: *Mar. 5, 2013

(54) METHODS OF MAKING POLYBORONIC COMPOUNDS AND COMPOSITIONS RELATED THERETO

(75) Inventors: Hong Sun, Houston, TX (US); Qi Qu, Spring, TX (US); Frances De Benedictis, Spring, TX (US); Jerry Edwin Pardue, Sugar Land, TX (US)

(73) Assignee: BJ Services Company, Houston, TX (US)

( * ) Notice: Subject to any disclaimer, the term of this patent is extended or adjusted under 35 U.S.C. 154(b) by 594 days.

This patent is subject to a terminal disclaimer.

(21) Appl. No.: 12/580,352

(22) Filed: Oct. 16, 2009

(65) Prior Publication Data

US 2010/0197966 A1 Aug. 5, 2010

Related U.S. Application Data

(63) Continuation-in-part of application No. 12/255,125, filed on Oct. 21, 2008, now Pat. No. 8,173,580.

(51) Int. Cl.
*C09K 8/60* (2006.01)
*C07F 5/02* (2006.01)

(52) U.S. Cl. ............ 564/9; 507/219; 507/233; 507/224; 507/261; 507/262; 507/267; 507/273; 166/308.1

(58) Field of Classification Search .................. None
See application file for complete search history.

(56) References Cited

U.S. PATENT DOCUMENTS

| | | | |
|---|---|---|---|
| 3,284,410 A | 11/1966 | Meinhardt | |
| 4,328,113 A | 5/1982 | Horodysky et al. | |
| 4,474,671 A | 10/1984 | Herd et al. | |
| 4,635,727 A | 1/1987 | Anderson et al. | |
| 5,305,832 A | 4/1994 | Gupta et al. | |
| 5,856,507 A * | 1/1999 | Polniaszek et al. | 548/241 |
| 5,972,850 A | 10/1999 | Nimerick | |
| 6,017,855 A | 1/2000 | Dawson et al. | |
| 6,060,436 A | 5/2000 | Snyder et al. | |
| 2002/0068826 A1* | 6/2002 | Song et al. | 544/335 |
| 2003/0135046 A1* | 7/2003 | Song et al. | 544/60 |
| 2006/0003900 A1* | 1/2006 | Hanes, Jr. | 507/203 |
| 2006/0089265 A1* | 4/2006 | Hanes et al. | 507/203 |

FOREIGN PATENT DOCUMENTS

GB 1545629 5/1979

OTHER PUBLICATIONS

PCT International Search Report and Written Opinion dated May 10, 2010, issued for PCT Application No. PCT/US2009/061174, filed Oct. 19, 2009.

Wiskur, et al, "pKa Values and Geometries of Secondary and Tertiary Amines Complexed to Boronic Acids—Implications for Sensor Design", Organic Letters, vol. 3, No. 9, 2001, pp. 1311-1314.

Lei, Cuiyue, et al., Crosslinking of Guar and Guar Derivatives, SPE Annual Technical Conference and Exhibition, Sep. 26-29, 2004, Houston, TX.

Lei, Cuiyue, et al., Fracturing-Fluid Crosslinking at Low Polymer Concentration, SPE Annual Technical Conference and Exhibition, Oct. 9-12, 2005, Dallas, TX.

* cited by examiner

*Primary Examiner* — John J Figueroa

(57) ABSTRACT

Polyboronic compounds and methods of making them are provided. The polyboronic compounds are useful as crosslinking agents. The polyboronic compounds are produced by contacting a polymeric amine with a trialkylborate in the presence of a solvent so that the resulting molecule has more than one B—N bond.

16 Claims, 2 Drawing Sheets

METHODS OF MAKING POLYBORONIC COMPOUNDS AND COMPOSITIONS RELATED THERETO

CROSS REFERENCE TO RELATED APPLICATIONS

The present application is a continuation-in-part patent application of U.S. patent application Ser. No. 12/255,125, filed Oct. 21, 2008, the contents of which are incorporated herein by reference in its entirety.

BACKGROUND OF THE INVENTION

1. Field of the Invention

The present invention relates to polyboronic compositions and methods of making them.

2. Description of the Related Art

Hydraulic fracturing techniques are widely used to enhance oil and gas production from subterranean formations. During hydraulic fracturing, a fluid is injected into a well bore under high pressure. Once the natural reservoir fracture gradient is exceeded, the fracturing fluid initiates a fracture in the formation that generally continues to grow during pumping. The treatment design generally requires the fluid to reach a maximum viscosity as it enters the fracture that affects the fracture length and width. The viscosity of most fracturing fluids is generated from water-soluble polysaccharides, such as galactomannans or cellulose derivatives. Linear gels that can be operated at ambient temperature do not have the necessary viscosity for proper proppant transferring at elevated temperature. The use of crosslinking agents or crosslinkers, such as borate, titanate, or zirconium (Zr) ions, can further increase the viscosity. The gelled fluid can be accompanied by a propping agent (i.e., proppant) that results in placement of the proppant within the fracture that has been produced. The proppant remains in the produced fracture to prevent the complete closure of the fracture and to form a conductive channel extending from the well bore into the formation being treated once the fracturing fluid is recovered.

Guar based fracturing fluids are the most commonly used fluids in reservoir stimulation. As indicated previously, stimulation of oil and, gas wells has been improved by the ability to crosslink fracturing fluids, such as guar. Crosslinking agents are used to significantly improve the viscosity of the system for various downhole conditions. Some common crosslinking agents include boron and zirconium or other metallic compounds. Boron crosslinked gels are more commonly used due to its reversibility to mechanical shearing and favorable environmental properties.

While boron and zirconium crosslinking agents are effective for many types of guar based fracturing fluids, a certain amount of the guar polymer is needed to achieve the viscosity necessary to fractionate the formation. It is desirable to use as little polymer as possible in a fracturing fluid so that the overall cost of the fracturing job is lower, less polymer residue remains in the fracture and the sand pack after breaking, and formation damage is minimized.

In view of the foregoing, a need exists for a crosslinking agent that would effectively increase the viscosity of the polymer, which simultaneously reduces the polymer loading as much as possible in fracturing fluids. A need also exists for compounds, such as polyboronic compounds, that can be prepared and have more than one B—N bond that helps with functions, such as crosslinking. Additionally, it would be advantageous if such crosslinking system is compatible with existing fracturing systems.

SUMMARY OF THE INVENTION

In view of the foregoing, crosslinked fracturing fluids and methods of fracturing subterranean formations are provided as embodiments of the present invention. The compositions and methods described herein are effective and allow for lower polymer loadings in fracturing jobs.

As an embodiment of the present invention, a fracturing fluid composition is provided. In this embodiment, the fracturing fluid includes a hydratable polymer capable of gelling in the presence of a crosslinking agent comprising a polyboronic compound.

Besides the compositional embodiments, methods of fracturing subterranean formations are also provided as embodiments of the present invention. For example, as another embodiment of the present invention, a method of fracturing a subterranean formation is provided. In this embodiment, water and a hydratable polymer capable of gelling are blended together and allowed to hydrate to form a hydrated polymer solution. Once the hydrated polymer solution is formed, a crosslinking agent comprising a polyboronic compound is added to the hydrated polymer solution to produce a crosslinked fracturing fluid. The crosslinked fracturing fluid is then injected into the subterranean formation to fracture the formation.

As another example, a method of fracturing a subterranean formation is provided as an embodiment of the present invention. In this embodiment, a fracturing fluid comprising a hydratable polymer is crosslinked by contacting the fracturing fluid with a polyboronic compound to produce a crosslinked fracturing fluid. The crosslinked fracturing fluid of the present invention has a higher viscosity when compared with the fracturing fluid being crosslinked with a conventional boric acid compound as a crosslinking agent at the same polymer loading. The crosslinked fracturing fluid is then injected into the subterranean formation to fracture the formation.

The resulting viscosity of the fracturing fluid of the present invention is higher than the resulting viscosity of fracturing fluids of the same polymer loading using conventional boric acid as the crosslinking agent. The increased viscosity of the crosslinked fracturing fluid of the present invention allows for a less amount of polymer to be used to achieve comparable results as prior art crosslinked fracturing fluids having higher polymer loadings. The resulting fracturing fluid of the present invention has a lower Ccc (critical crosslinking concentration) than the same polymer being crosslinked with conventional boric acid crosslinking agent.

In addition to the crosslinking agent, as an embodiment of the present invention, polyboronic compounds and methods of making them are provided as embodiments of the present invention. The polyboronic compounds and methods of making them described herein can be used as crosslinking agents in compositions and methods described herein. It is believed that they can also be used in other applications, as well.

Figure 1:
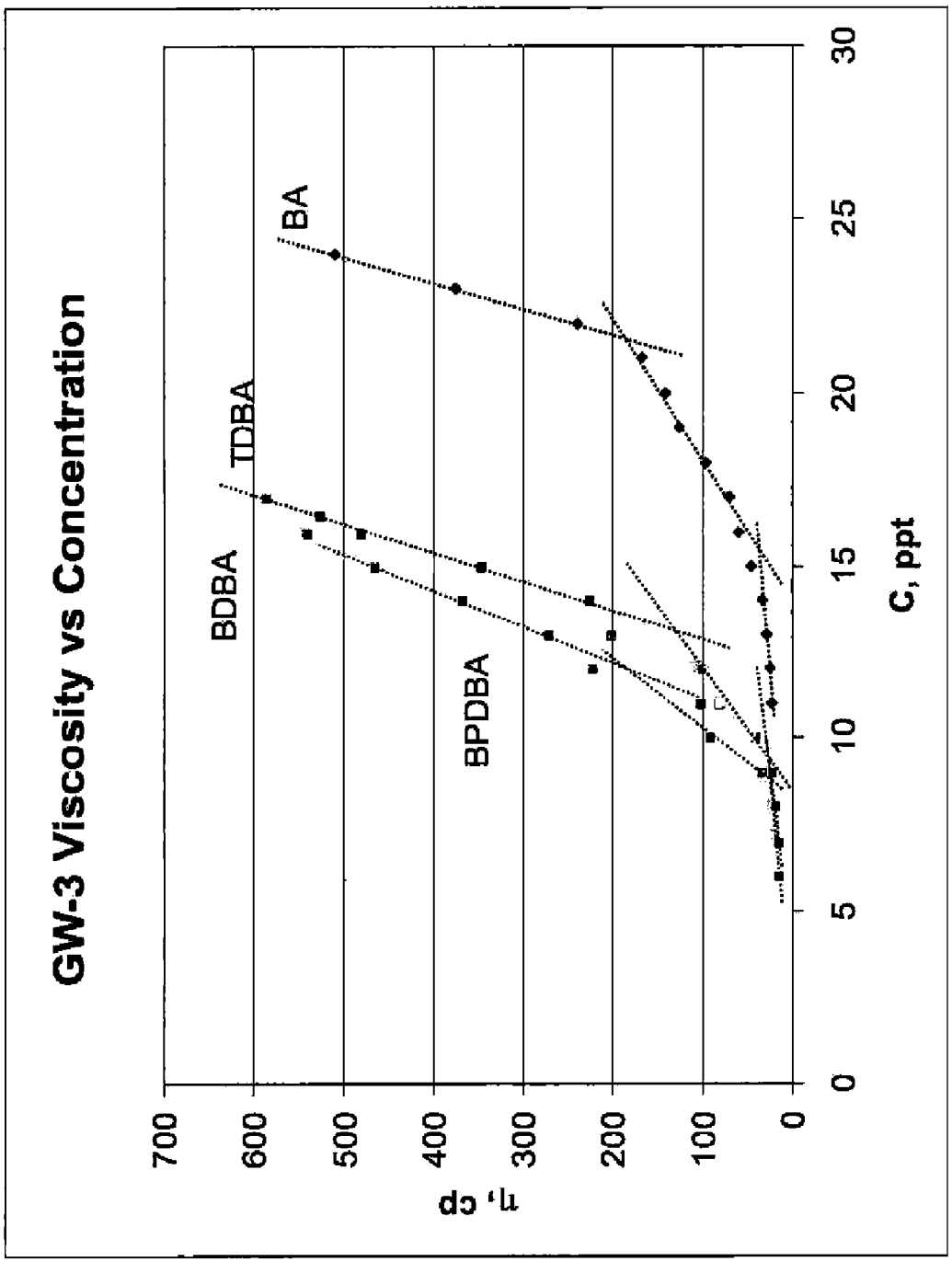
FIG. 1 is a chart showing the viscosity (cP) of GW-3 guar at various concentrations (ppt) using various crosslinking agents in accordance with embodiments of the present invention and in accordance with prior art embodiments.

While the invention is susceptible to various modifications and alternative forms, specific embodiments have been shown by way of example in the drawings and will be described in detail herein. However, it should be understood that the invention is not intended to be limited to the particular forms disclosed. Rather, the intention is to cover all modifications, equivalents and alternatives falling within the spirit and scope of the invention as defined by the appended claims.

DESCRIPTION OF ILLUSTRATIVE EMBODIMENTS

Illustrative embodiments of the invention are described below as they might be employed in the operation and in the treatment of oilfield applications. In the interest of clarity, not all features of an actual implementation are described in this specification. It will of course be appreciated that in the development of any such actual embodiment, numerous implementation-specific decisions must be made to achieve the developers' specific goals, which will vary from one implementation to another. Moreover, it will be appreciated that such a development effort might be complex and time-consuming, but would nevertheless be a routine undertaking for those of ordinary skill in the art having the benefit of this disclosure. Further aspects and advantages of the various embodiments of the invention will become apparent from consideration of the following description.

As an embodiment of the present invention, a crosslinked fracturing fluid composition is provided. In this embodiment, the fracturing fluid includes a hydratable polymer capable of gelling in the presence of a crosslinking agent comprising a polyboronic compound. Typical hydratable polymers include, not limited to, polysaccharide, guar gum, guar gum derivatives, locust bean gum, karaya gum, carboxymethyl cellulose, carboxymethylhydroxyethyl cellulose, hydroxyethyl cellulose, or combinations thereof. Various types of polyboronic compounds can be used in embodiments of the present invention, as described herein. Conventional boron crosslinking agents used in hydraulic fracturing fluids are generally composed of borate salts or esters. The polyboronic compounds of the present invention are more effective when compared to the conventional boron crosslinking agents, which enables users to lower the polymer loading for fracturing jobs.

Besides the compositional embodiments, methods of fracturing subterranean formations are also provided as embodiments of the present invention. For example, as another embodiment of the present invention, a method of fracturing a subterranean formation is provided. In this embodiment, water and a hydratable polymer capable of gelling in the presence of a crosslinking agent are blended together and allowed to hydrate to form a hydrated polymer solution. Once the hydrated polymer solution is formed, a crosslinking agent comprising a polyboronic compound is added to the hydrated polymer solution to produce a crosslinked fracturing fluid. The crosslinked fracturing fluid is then injected into the subterranean formation to fracture the formation.

As another example, a method of fracturing a subterranean formation is provided as an embodiment of the present invention. In this embodiment, a fracturing fluid comprising a hydratable polymer is crosslinked by contacting the fracturing fluid with a polyboronic compound to produce a crosslinked fracturing fluid. The crosslinked fracturing fluid of the present invention has a higher viscosity when compared with the fracturing fluid being crosslinked with conventional boric acid crosslinking agents. The crosslinked fracturing fluid is then injected into the subterranean formation to fracture the formation.

The amounts of the components within the fracturing fluid can be varied in various embodiments of the present invention. For example, the polyboronic compound can be present in a range of about 0.02 vol. % to about 0.5 vol. % of the fracturing fluid composition; alternatively, in a range of about 0.10 vol. % to about 0.25 vol. %. In an aspect, the polyboronic compounds can be present in a range that is effective for achieving the desired viscosity of the resulting fracturing fluid, as will be apparent to those of skill in the art.

The methods and compositions described herein can be used with various types of fracturing fluid systems. The hydratable polymer can be varied depending upon the needs of a particular fracturing job. For example, the hydratable polymer can be guar gum, guar gum derivatives, locust bean gum, karaya gum, carboxymethyl cellulose, carboxymethylhydroxyethyl cellulose, hydroxyethyl cellulose, or combinations thereof. Other suitable hydratable polymers that are compatible with the methods and compositions described herein can be used and are to be considered within the scope of the present invention.

The methods and the compositions described herein are very efficient and have a lower polymer loading when compared with the same polymer system being crosslinked using conventional crosslinking agents, such as boric acid. The methods and compositions described herein can have a higher viscosity when compared with the same amount of polymer that has been crosslinked with conventional crosslinking agents, such as boric acid. In an aspect, the fracturing fluid composition of the present invention has a Ccc of less than about 12 ppt. In another aspect, the fracturing fluid composition of the present invention has a Ccc less than about 15.5 ppt.

In an aspect, various compounds can be used as the polyboronic compound used in embodiments of the present invention. Suitable polyboronic compounds can include 2,5-thiophenediboronic acid (TDBA), 1,4-benzenediboronic acid (BDBA), 4,4'-biphenyldiboronic acid (BPDBA), or combinations thereof. In an aspect, the polyboronic compounds can include compounds having the following structures:

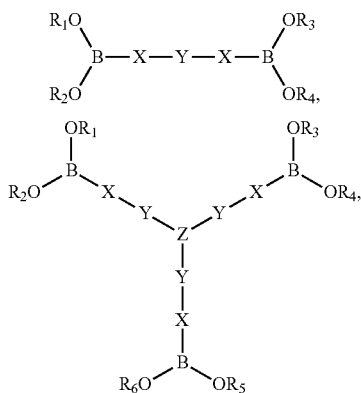

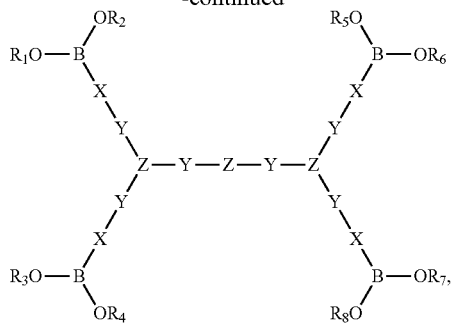

or combinations thereof, wherein, $R_1$-$R_8$ can be hydrogen, alkyl group, alkenyl group, alkynyl group, aryl group, or combinations thereof. $R_1$-$R_8$ can be, but is not required to be, identical and they can also be from the same fragment to form ring structures (such as, $R_1$, $R_2$=—$CH_2CH_2$—; —$C(CH_3)_2C(CH_3)_2$—, etc); X can be carbon, nitrogen, silicon, or combinations thereof. In an aspect, a compound with X being nitrogen to incorporate multiple boron atoms into the structure by the chemical bonding between N and B atoms is acceptable. Y can be a spacer, which can be straight chain of —($CH_2$)—, straight chain with pendant(s), straight chain with branching, aromatic ring(s) directly connected, aromatic ring(s) indirectly connected, fused aromatic rings, heterocyclic ring(s) directly connected, heterocyclic ring(s) indirectly connected, fused heterocyclic rings, aliphatic ring(s) directly connected, aliphatic ring(s) indirectly connected, fused aliphatic rings, or combinations thereof. For example, Y can be phenylene, biphenylene, triphenylene, fluorene, fluorenone, naphthalene, methylene bisphenylene, stilbene, or combinations thereof. In an aspect, X can also be part of Y when Y has ring structure(s). Z can be carbon, silicon, oxygen, nitrogen, alkyl group, alkenyl group, alkynyl group, aromatic ring(s), aliphatic ring(s), heterocyclic ring(s), or combinations thereof. Z can also be a metal atom, such as, Al, Zr, Ti, Zn, or the like connected to other parts of the structure via chelation and/or other chemical interactions. Z can also be a fragment of Y. The general structure of suitable polyboronic compounds can be further extended to dendrimeric "poly" boronic compounds. Other suitable types of polyboronic compounds will be understood by those of skill in the art and are to be considered within the scope of the present invention.

The polyboronic compounds belong to a different type of chemistry from conventional boric acid, its ester derivatives and polyboric acids and their salts. In the chemistry nature of these boric acids or their derivatives, boron atoms are not connected to any atom other than oxygen, which leads to hydrolyzation in aqueous solution and release of boric acid. When used as crosslinking agents, the actual crosslinking species is boric acid after hydrolysis of borate esters or polyborates. When boron atom is connected to at least one atom other than the oxygen atoms, especially carbon or nitrogen, the corresponding compounds are called boronic acids (or boronic esters) and they are different compounds and possess different chemical properties. When they contact water or base, even at elevated temperatures, the B—C (or B—N, B—Si, etc.) bond will not hydrolyze, and therefore the active crosslinking species is not boric acid, but polyboronic compounds instead. When these diboronic or polyboronic compounds are used as crosslinking agents, they will provide two or more boron atom sites, each is capable of being chelated with the two cis-hydroxyls in the backbone of the hydratable polymers. Therefore, a triboronic compound can crosslink three polysaccharide chains via three boron atoms within one crosslinking agent molecule. In other words, the polyboronic species are the crosslinking agents, not boric acid hydrolyzed from corresponding esters, as shown in prior art, as delayed boric acid crosslinking agents. In an aspect, when N is attached to B, to form stable $(OR)_2BNHRHNB(OR)_2$ structure is particularly preferred.

Besides the polymer and crosslinking agents described herein, various additives can be useful in the present invention. Additives used in the oil and gas industry and known in the art, including but not limited to, corrosion inhibitors, non-emulsifiers, iron control agents, delay additives, silt suspenders, flowback additives, pH adjusting agents, clay stabilizer, surfactants, and gel breakers, can also be used in embodiments of the present invention. Proppants including, but not limited to, frac sand, resin coated sand, quartz sand grains, ceramic proppant, tempered glass beads, rounded walnut shell fragments, aluminum pellets, and nylon pellets at desired size can also be used. Proppant is typically used in concentrations that range between about 1 pound per gallon of the fracturing fluid composition to about 8 pounds per gallon of the fracturing fluid composition. Other suitable additives useful in the present invention will be apparent to those of skill in the art and are to be considered within the scope of the present invention.

The fracturing fluid of the present invention can be used by pumping the fluid into a well bore penetrating the subterranean formation to be fractured. The fracturing fluid is injected at a rate sufficient to fracture the formation and to place proppant into the fracture.

As another advantage of the present invention, lower loadings of polymer can be used to obtain equivalent fracturing fluid performance at reduced overall treatment costs. Reduced polymer loadings can also result in less damage to the surrounding subterranean formation after the fracturing treatment. Guar based polymers are attributed with causing damage to the fracture sand pack and reducing the effective fracture width. The present invention permits substantial reduction in the amount of polymer injected into the formation while maintaining optimal fluid properties for creating the fracture.

C*, C**, and Ccc are often used as the leading indexes to represent the efficiency of a crosslinked polymer fluid. C*, C** and Ccc depend on the type of polymer being used, as well as, possibly the type of crosslinking agent used. As used herein, the term "Ccc" is used to describe the critical crosslinking concentration for polymer chains, as will be understood by those of skill in the art. The term "Ccc" is generally considered to be minimum polymer concentration where the fluid is able to be crosslinked. It was proposed by others that Ccc is largely independent on the type of crosslinking agent used. As a result of the findings related to the present invention, it was discovered that the conventional theory is not necessarily true. The examples described herein show that the type of crosslinking agent used can affect Ccc, which is contrary to what was previously believed. The structures of the crosslinking agents of the present invention lowered the Ccc of guar polymer so significantly that the polymer solutions can be effectively crosslinked at concentrations much lower than widely accepted Ccc values.

In addition to the crosslinking agent and related compositions and methods, polyboronic compounds and methods of making them are also provided as embodiments of the present invention. The polyboronic compounds and methods of making them described herein can be used as crosslinking agents in the compositions and methods described herein. It is believed that they can also be used in other applications, as well.

In an embodiment, a method of making a polyboronic compound is provided. In this embodiment, a polymeric amine is contacted with a trialkylborate in the presence of a solvent to produce the polyboronic compound having more than one B—N bond. Excess trialkylborate can be used. Alternatively, an insufficient amount of trialkylborate can be used.

In an aspect, the polyboronic compound can have the following structures:

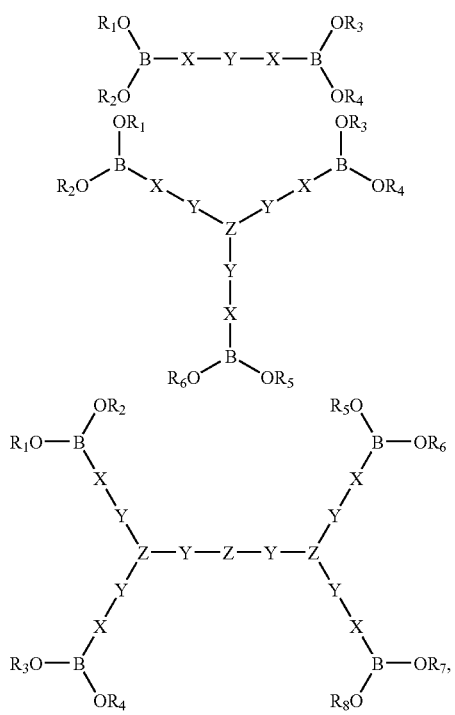

or combinations thereof, wherein $R_1$-$R_8$ is hydrogen, alkyl group, alkenyl group, alkynyl group, aryl group, or combinations thereof, X is nitrogen; Y is a straight chain of —$(CH_2)$—, a straight chain with pendant(s), a straight chain with branching, aromatic ring(s) directly connected, aromatic ring(s) indirectly connected, fused aromatic rings, heterocyclic ring(s) directly connected, heterocyclic rings) indirectly connected, fused heterocyclic rings, aliphatic ring(s) directly connected, aliphatic ring(s) indirectly connected, fused aliphatic rings, or combinations thereof; and Z is carbon, silicon, oxygen, nitrogen, alkyl group, alkenyl group, alkynyl group, aromatic ring(s), aliphatic ring(s), heterocyclic ring(s), a metal atom, or combinations thereof.

As with other embodiments of the present invention, various types of polymeric amines can be used to produce the polyboronic compounds of the present invention. In an aspect, the polymeric amine can include ethylenediamine, diethylene triamine (DETA), triethylenetetramine (TETA), tetraethylenepentamine (TEPA), 1,2-, 1,3-propylenediamine, dipropylenetriamine, tripropylenetetramine, tetrapropylenepentamine, ethylene propylene triamine, ethylene dipropylene tetramine, diethylene propylene tetramine, ethylene tripropylene pentamine, diethylene dipropylene pentamine, triethylene propylene pentamine, polyethylenimine (e.g., Epomin® from Nippon Shokubai, Lupasol™ from BASF, Lupamine™ from BASF, etc.), poly(ethyleneoxy)amines, poly(propyleneoxy)amines (i.e., Jeffamine® T-403 from Huntsman Corporation, Polyetheramine T-5000 from BASF, etc.) or combinations thereof. Other suitable types of polymeric amines that can be used in the present invention will be apparent to those of skill in the art and are to be considered within the scope of the present invention.

Besides varying the types of polymeric amines that can be used in the present invention, the types of trialkylborates suitable in the present invention can also be varied. For example, in an aspect, the trialkylborate can include trimethylborate, triethylborate, tripropylborate, triisopropyl borate, tributyl borate, tri(tert-butyl)borate, or combinations thereof. Other suitable types of trialkylborates that can be used in the present invention will be apparent to those of skill in the art and are to be considered within the scope of the present invention.

Similarly to the polymeric amines and the trialkylborates, the types of solvents that can be used in the present invention can also be varied. For example, in an aspect, the solvent can include methanol, ethanol, propanol, 2-propanol, butanol, 2-butanol, tert-butanol, or combinations thereof. Other suitable types of solvents that can be used in the present invention will be apparent to those of skill in the art and are to be considered within the scope of the present invention.

The polyboronic compounds of the present invention have more than one B—N in the structure. The number of B—N bonds can be varied depending upon the type of polymeric amine or trialkylborate selected to produce the polyboronic compound. In an aspect, the polyboronic compound can include at least two B—N bonds. In another aspect, the polyboronic compound can include as many B—N bonds as there are N atoms in the polymeric amine.

As another embodiment of the present invention, another method of making a polyboronic compound is provided. In this embodiment, a polymeric amine is contacted with a trialkylborate in the presence of a solvent to produce the polyboronic compound. The polymeric amine comprises ethylenediamine, diethylene triamine (DETA), triethylenetetramine (TETA), tetraethylenepentamine (TEPA), 1,2-, 1,3-propylenediamine, dipropylenetriamine, tripropylenetetramine, tetrapropylenepentamine, ethylene propylene triamine, ethylene dipropylene tetramine, diethylene propylene tetramine, ethylene tripropylene pentamine, diethylene dipropylene pentamine, triethylene propylene pentamine, polyethylenimine, poly(ethyleneoxy)amines, poly(propyleneoxy)amines or combinations thereof; and the polyboronic compound comprises

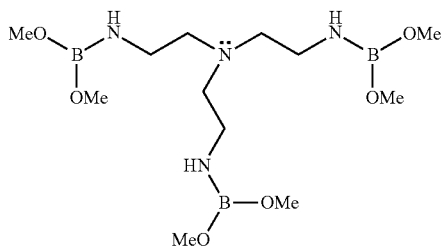 [SMILES: COB(NCCN(CCNB(OC)OC)CCNB(OC)OC)OC]

and its other ester analogs, such as ethyl boronate, etc. As with other embodiments of the present invention, excess trialkylborate can be used during the step of contacting the polymeric amine with the trialkylborate. Alternatively, an insufficient amount of trialkylborate can be used.

As yet another embodiment of the present invention, a polyboronic compound having more than one B—N bond that provides more than one borate reaction (crosslinking) site is provided. In an aspect, the polyboronic compound comprising:

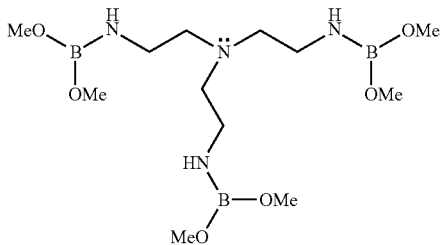 [SMILES: COB(NCCN(CCNB(OC)OC)CCNB(OC)OC)OC]

and its other ester analogs, such as ethyl boronate, etc.

In embodiments of the present invention, the polyboronic compound can include

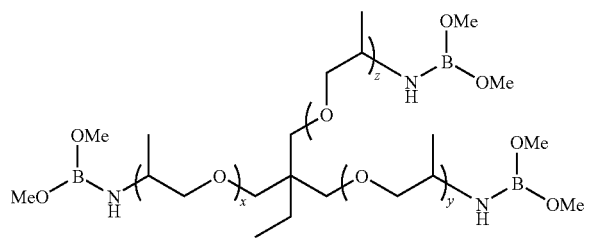

wherein the sum of x, y and z is 5 or 6. Besides this compound, its other ester analogs can also be included, such as ethyl boronate, as will be apparent to those of skill in the art and are to be considered within the scope of the present invention.

In an aspect, the polyboronic compound can include

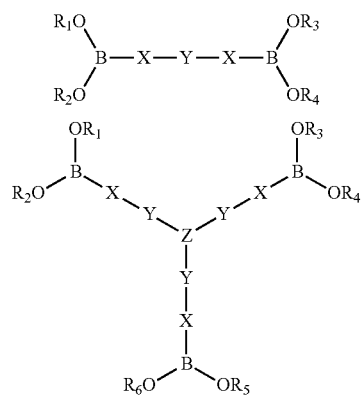

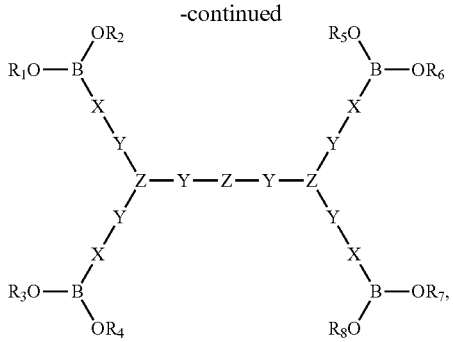

or combinations thereof, wherein $R_1$-$R_8$ is hydrogen, alkyl group, alkenyl group, alkynyl group, aryl group, or combinations thereof; X is nitrogen; Y is a straight chain of —($CH_2$)—, a straight chain with pendant(s), a straight chain with branching, aromatic ring(s) directly connected, aromatic ring(s) indirectly connected, fused aromatic rings, heterocyclic ring(s) directly connected, heterocyclic ring(s) indirectly connected, fused heterocyclic rings, aliphatic ring(s) directly connected, aliphatic ring(s) indirectly connected, fused aliphatic rings, or combinations thereof; and Z is carbon, silicon, oxygen, nitrogen, alkyl group, alkenyl group, alkynyl group, aromatic ring(s), aliphatic ring(s), heterocyclic ring(s), a metal atom, or combinations thereof.

The polyboronic compound can be produced by contacting a polymeric amine with a trialkylborate in the presences of a solvent. In an aspect, the polymeric amine can be ethylenediamine, diethylene triamine (DETA), triethylenetetramine (TETA), tetraethylenepentamine (TEPA), 1,2-, 1,3-propylenediamine, dipropylenetriamine, tripropylenetetramine, tetrapropylenepentamine, ethylene propylene triamine, ethylene dipropylene tetramine, diethylene propylene tetramine, ethylene tripropylene pentamine, diethylene dipropylene pentamine, triethylene propylene pentamine, polyethylenimine, poly(ethyleneoxy)amines, poly(propyleneoxy) amines, or combinations thereof; and the trialkylborate can be trimethylborate, triethylborate, tripropylborate, triisopropyl borate, tributyl borate, tri(tert-butyl)borate, or combinations thereof.

EXAMPLES

The following examples are included to demonstrate the use of compositions in accordance with embodiments of the present invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the scope of the invention.

Example 1

Example 1 was used to determine Ccc and to test the effectiveness of the crosslinking agents made in accordance with embodiments of the present invention. 25 ppt (0.3%) solution of guar gum (GW-3, which is commercially available from BJ Services Company) was prepared by hydrating GW-3 powder. After at least 30 minutes, the solution was systematically diluted to obtain 6, 7, 8, 9, 10, 11, 12, 13, 14, 15, 16, 17, 18, 19, 20, 21, 22, 23, 24 ppt solutions. Other additives (such as buffer, clay stabilizer, and bactericide) were added to the GW-3 guar solution. The crosslinking agents made in accordance with embodiments of the present invention were then added by mixing. The polymer/crosslinking agent ratio was kept constant. The viscosity of the crosslinked gel was measured on Fann 35 instrument at room temperature. The polymer/crosslinking agent ratios were as follows:

| TDBA/GW-3 = 0.079 | BDBA/GW-3 = 0.039 | BPDBA/GW-3 = 0.056 | BA/GW-3 = 0.022 |
| TDBA/GW-45 = 1.10 | BDBA/GW-45 = 1.13 | | BA/GW-45 = 0.2233 |

Figure 2:
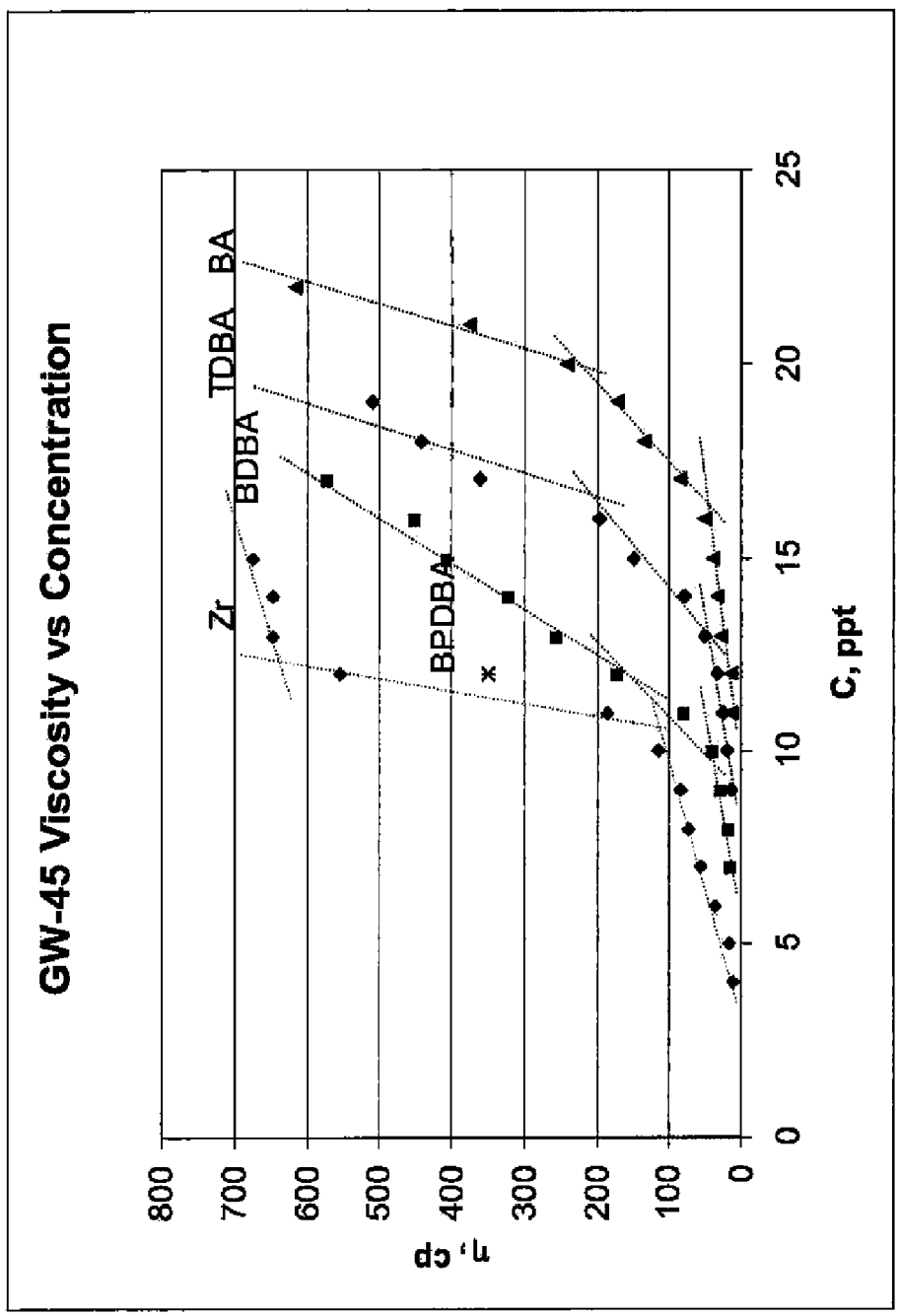
FIG. 2 is a chart showing the viscosity (cP) of GW-45 guar derivative at various concentrations (ppt) using various crosslinking agents in accordance with embodiments of the present invention and in accordance with prior art embodiments.

The ratios were kept constant within each crosslinking agent to obtain systematic readings. The viscosity was plotted against the concentration to observe changes in viscosity versus concentration change, as shown in FIGS. 1 and 2. As concentration increases, a change in slope occurs. The interception of the slopes of the two regions defines Ccc.

Example 2

The Ccc values were calculated for two different types of guar fracturing fluids, GW-3 and GW-45, that were crosslinked with four different types of crosslinking agents. GW-3 and GW-45 are guar based polymers commercially available from BJ Services Company. As can be seen in Table 1, a lower Ccc was obtained using the various polyboronic compounds (i.e., TDBA, BDBA, and BPDBA) when compared to the same guar polymers being crosslinked with conventional boric acid (BA). The results of this example show that the type of crosslinking agent can greatly affect the Ccc, which is contrary to what is conventionally accepted in the industry.

TABLE 1

| | $C_{cc}$, ppt | | | |
|---|---|---|---|---|
| Polymer | BA | TDBA | BDBA | BPDBA |
| GW-3 | 15 | 9 | 8.5 | 8 |
| GW-45 | 15.5 | 12 | 8.5 | |

Example 3

In this example, the viscoelastic properties (n') and viscosities (cP) of two crosslinked guar polymer systems were compared. 15 ppt of GW-3 was crosslinked with 0.27 mmol BPDBA at 150° F. and compared with a typical crosslinked system that was prepared by crosslinking 20 ppt of GW-3 with CXB-10, which is commercially available from BJ Services Company. As shown in Table 2, the results clearly demonstrate that these polyboronic compounds used in embodiments of the present invention can effectively lower polymer loading for fracturing stimulation. The reduction of the polymer loading is related to the size of the group separating the two boronic acids.

TABLE 2

| | 15 ppt GW-3, 0.27 mmol BPDBA | | | | 20 ppt GW-3, 1 gpt CXB-10 | | | |
|---|---|---|---|---|---|---|---|---|
| | | Viscosity (cP) at | | | | Viscosity (cP) at | | |
| Time, min | n' | 40 sec$^{-1}$ | 100 sec$^{-1}$ | 170 sec$^{-1}$ | n' | 40 sec$^{-1}$ | 100 sec$^{-1}$ | 511 sec$^{-1}$ |
| 2.1 | 0.671 | 481 | 356 | 299 | 0.389 | 1855 | 1060 | 391 |
| 32.1 | 0348 | 582 | 320 | 227 | 0.533 | 349 | 228 | 106 |
| 62.1 | 0.358 | 665 | 369 | 263 | 0.871 | 343 | 305 | 247 |
| 92.1 | 0.276 | 694 | 358 | 244 | 0.753 | 317 | 253 | 169 |
| 122.1 | 0.443 | 489 | 293 | 218 | 0.814 | 314 | 265 | 195 |

Example 4

Example 4 illustrates one embodiment of the synthetic preparation of a polyboronic compound having the following structure. This example can be used to illustrate how polyboronic compounds are generally synthesized. The synthesis scheme can be extended to other type of polyboronic compounds.

In this example, a 150 mL 3-necked round bottom flask was equipped with a temperature indicator, a pressure-equalizing addition funnel and a reflux condenser guarded with a CaCl$_2$ drying tube. Into the flask was added 7.3 g tris(2-aminoethyl)amine, followed with 15 g anhydrous MeOH. Under nitrogen, 20.8 g freshly distilled trimethyl borate was transferred into the addition funnel and was then diluted with 6.9 g anhydrous MeOH. Under magnetic agitation, the trimethyl borate solution was added drop by drop into the flask at a temperature below 40° C. After the completion of the addition, the resultant solution was allowed to stand at room temperature for 30 minutes and then heated to reflux for at least 4 hours. The resulting compound

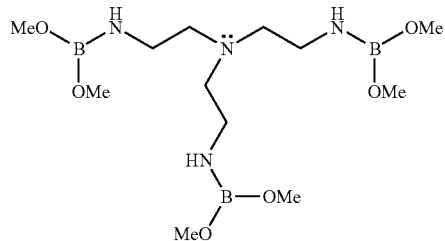 [SMILES: COB(NCCN(CCNB(OC)OC)CCNB(OC)OC)OC]

(and its other ester analogs, such as ethyl boronate, etc.) can be used as a crosslinking agent in accordance with embodiments of the present invention, such as those described in Example 5.

Example 5

In Example 5, the viscoelastic properties (n') and viscosities (cP) of two crosslinked guar polymer systems were compared. 25 ppt of GW-3 was crosslinked with 0.4 mmol compound prepared in Example 4 and 4 gpt 25% sodium hydroxide (NaOH) at 150° F. and compared with an optimized crosslinked system that was prepared by crosslinking 25 ppt of GW-3 with CXB-10, which is commercially available from BJ Services Company. As shown in Table 3, the results clearly demonstrate that these polyboronic compounds used in embodiments of the present invention can effectively lower polymer loading for fracturing stimulation.

TABLE 3

| | 25 ppt GW-3, 0.4 mmol XLB | | | | 25 ppt GW-3, 3 gpt CXB-10 | | | |
|---|---|---|---|---|---|---|---|---|
| | | Viscosity (cP) at | | | | Viscosity (cP) at | | |
| Time, min | n' | 40 sec$^{-1}$ | 100 sec$^{-1}$ | 170 sec$^{-1}$ | n' | 40 sec$^{-1}$ | 100 sec$^{-1}$ | 170 sec$^{-1}$ |
| 2.1 | 0.4827 | 1091 | 568 | 389 | 0.3783 | 3924 | 2220 | 1596 |
| 32.1 | 0.3170 | 1648 | 923 | 660 | 0.2807 | 1354 | 700 | 478 |
| 62.1 | 0.4061 | 1646 | 1047 | 806 | 0.3011 | 1332 | 702 | 485 |
| 92.1 | 0.3914 | 1433 | 918 | 709 | 0.3098 | 1453 | 772 | 535 |
| 122.1 | 0.4074 | 1335 | 824 | 623 | 0.4278 | 1355 | 802 | 592 |
| 152.1 | 0.5785 | 1264 | 883 | 717 | 0.3857 | 1166 | 664 | 479 |
| 182.1 | 0.6394 | 1169 | 872 | 736 | 0.1443 | 1337 | 610 | 388 |

All of the compositions and/or methods disclosed and claimed herein can be made and executed without undue experimentation in light of the present disclosure. While the compositions and methods of this invention have been described in terms of preferred embodiments, it will be apparent to those of skill in the art that variations can be applied to the compositions and/or methods and in the steps or in the sequence of steps of the methods described herein without departing from the concept, spirit and scope of the invention. More specifically, it will be apparent that certain agents that are chemically related can be substituted for the agents described herein while the same or similar results would be achieved. All such similar substitutes and modifications apparent to those skilled in the art are deemed to be within the scope and concept of the invention.

What is claimed is:

1. A method of making a polyboronic compound comprising contacting a polymeric amine with a trialkylborate in the presence of a solvent to produce the polyboronic compound having more than one B—N bond, wherein the polyboronic compound comprises:

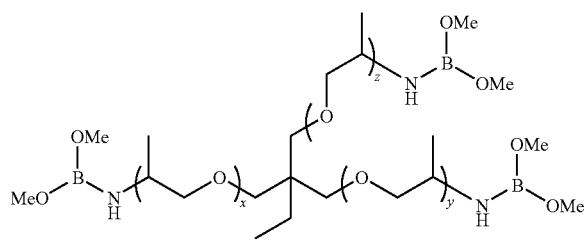

wherein x+y+z=5 or 6.

2. The method of claim 1, wherein the polymeric amine comprises ethylenediamine, diethylene triamine (DETA), triethylenetetramine (TETA), tetraethylenepentamine (TEPA), 1,2-, 1,3-propylenediamine, dipropylenetriamine, tripropylenetetramine, tetrapropylenepentamine, ethylene propylene triamine, ethylene dipropylene tetramine, diethylene propylene tetramine, ethylene tripropylene pentamine, diethylene dipropylene pentamine, triethylene propylene pentamine, polyethylenimine, poly(ethyleneoxy)amines, poly(propyleneoxy)amines, or combinations thereof.

3. The method of claim 1, wherein the trialkylborate comprises trimethylborate, triethylborate, tripropylborate, triisopropyl borate, tributyl borate, tri(tert-butyl)borate, or combinations thereof.

4. The method of claim 1, wherein the solvent comprises methanol, ethanol, propanol, 2-propanol, butanol, 2-butanol, tent-butanol, or combinations thereof.

5. The method of claim 1, wherein the step of contacting the polymeric amine with the trialkylborate includes contacting the polymeric amine with an excess amount of trialkylborate or an insufficient amount of trialkylborate.

6. The method of claim 1, wherein the polyboronic compound comprises at least two B—N bonds.

7. The method of claim 1, wherein the polyboronic compound comprises as many B—N bonds as there are N atoms in the polymeric amine.

8. A method of making a polyboronic compound comprising contacting a polymeric amine with a trialkylborate in the presence of a solvent to produce the polyboronic compound, wherein the polymeric amine comprises ethylenediamine, diethylene triamine (DETA), triethylenetetramine (TETA), tetraethylenepentamine (TEPA), 1,2-, 1,3-propylenediamine, dipropylenetriamine, tripropylenetetramine, tetrapropylenepentamine, ethylene propylene triamine, ethylene dipropylene tetramine, diethylene propylene tetramine, ethylene tripropylene pentamine, diethylene dipropylene pentamine, triethylene propylene pentamine, polyethylenimine, poly(ethyleneoxy)amines, poly(propyleneoxy)amines, or combinations thereof, wherein the polyboronic compound comprises:

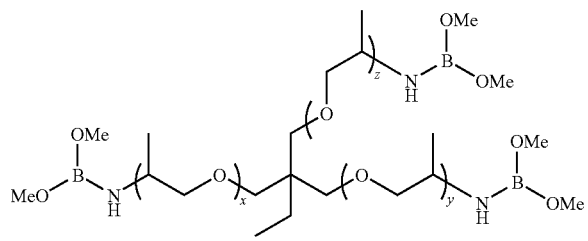

wherein x+y+z=5 or 6.

9. The method of claim 8, wherein the trialkylborate comprises trimethylborate, triethylborate, tripropylborate, triisopropyl borate, tributyl borate, tri(tert-butyl)borate, or combinations thereof.

10. The method of claim 8, wherein the solvent comprises methanol, ethanol, propanol, 2-propanol, butanol, 2-butanol, tert-butanol, or combinations thereof.

11. The method of claim 8, wherein the polyboronic compound has as many B—N bonds as an alkyl group of the trialkylborate has carbon molecules.

12. The method of claim 8, wherein the step of contacting the polymeric amine with the trialkylborate includes contacting the polymeric amine with excess or an insufficient amount of trialkylborate.

13. A polyboronic compound having more than one B—N bond that provides more than one borate reaction crosslinking site, wherein the polyboronic compound comprises:

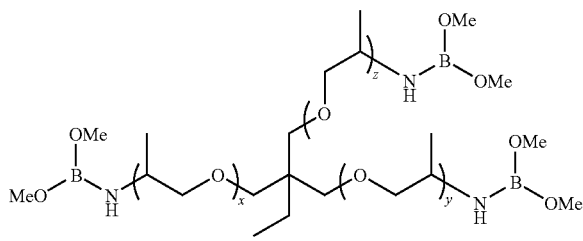

wherein x+y+z=5 or 6.

14. The polyboronic compound of claim 13 produced by contacting a polymeric amine with a trialkylborate in the presences of a solvent.

15. The polyboronic compound of claim 14, wherein the polymeric amine is ethylenediamine, diethylene triamine (DETA), triethylenetetramine (TETA), tetraethylenepentamine (TEPA), 1,2-,1,3-propylenediamine, dipropylenetriamine, tripropylenetetramine, tetrapropylenepentamine, ethylene propylene triamine, ethylene dipropylene tetramine, diethylene propylene tetramine, ethylene tripropylene pentamine, diethylene dipropylene pentamine, triethylene propylene pentamine, polyethylenimine, poly(ethyleneoxy) amines, poly(propyleneoxy)amines, or combinations thereof.

16. The polyboronic compound of claim 14, wherein the trialkylborate is trimethylborate, triethylborate, tripropylborate, triisopropyl borate, tributyl borate, tri(tert-butyl)borate, or combinations thereof.

* * * * *